(12) United States Patent
Perdew, Jr.

(10) Patent No.: US 6,727,210 B1
(45) Date of Patent: Apr. 27, 2004

(54) CLEANSING COMPOSITION, DEVICE AND METHOD

(76) Inventor: Donald E. Perdew, Jr., 7058 Bedford Valley Rd., Bedford, PA (US) 15522

( * ) Notice: Subject to any disclaimer, the term of this patent is extended or adjusted under 35 U.S.C. 154(b) by 0 days.

(21) Appl. No.: 10/439,778

(22) Filed: May 15, 2003

(51) Int. Cl.⁷ ................................................ C11D 17/00
(52) U.S. Cl. ...................... 510/130; 510/159; 510/480; 510/499; 510/504
(58) Field of Search ................................ 510/130, 159, 510/480, 499, 504

(56) References Cited

U.S. PATENT DOCUMENTS

| | | | |
|---|---|---|---|
| 6,153,208 A | * 11/2000 | McAtee et al. | 424/402 |
| 6,338,855 B1 | * 1/2002 | Albacarys et al. | 424/409 |
| 2002/0086039 A1 | * 7/2002 | Lee et al. | 424/401 |
| 2003/0162838 A1 | * 8/2003 | Yumioka et al. | 514/625 |
| 2003/0190302 A1 | * 10/2003 | Frantz et al. | 424/70.24 |

* cited by examiner

*Primary Examiner*—Necholus Ogden

(57) ABSTRACT

A composition, device and associated method of using the composition for use in cleaning the epidermis of a user. The composition comprises water; aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate. The device comprises a pouch containing a towelette containing the composition of the present invention. The method of using comprises the steps of obtaining, opening, pulling, and wiping.

20 Claims, 3 Drawing Sheets

| INGREDIENTS |
| --- |
| ALOE EXTRACT |
| CITRIC ACID |
| DISODIUM EDTA |
| PEG-60 LANOLIN |
| POTASSIUM SORBATE |
| PROPYLENE GLYCOL |
| QUATERNIUM-52 |
| SD ALCOHOL |
| WATER |
| BENZETHONIUM CHLORIDE |
| PUMICE |
| METHYCHLORIDSOTHIAZOLINONE |
| METHYLISOTHIAZALINONE |
| DEGREASER |
| TRIETHANOLAMINE |
| TOCOPHERYLACETATE |
| SCENT |

FIG. 1

CLEANSING COMPOSITION, DEVICE AND METHOD

FIELD OF THE INVENTION

The present invention relates chemical compositions, more particularly to a cleansing composition, device and associated method for use to clean the epidermis of a user.

DESCRIPTION OF THE PRIOR ART

It is important to clean oneself to prevent infections as well as to minimize the spread of diseases. Many agree that cleanliness is next to godliness. Therefore, a cleaning composition, device and associated method for use in cleaning the epidermis of a user is useful.

A wide variety of cleaning apparatuses is currently available on the commercial market and an even larger number of these types of devices are known in the art of cleaning apparatuses, for example, the wet wiper natural acid preservation system disclosed by Johnson in U.S. Pat. No. 4,732,797; the nonwoven wipe impregnating composition disclosed by Pregozen in U.S. Pat. No. 5,141,803; the hand wipe solution disclosed by Khan in U.S. Pat. No. 5,512,199; the antimicrobial compositions and wet wipes including the same disclosed by Cole in U.S. Pat. No. 5,888,524; the wet wipe with non-aqueous, oil-based solvent for industrial cleaning disclosed by Strout et al. in U.S. Pat. No. 6,136,775; and the pre-moistened disinfecting towellette disclosed by Harris in U.S. Pat. No. D396,982.

While all of the above-described devices fulfill their respective, particular objectives and requirements, the aforementioned patents do not describe a cleansing composition comprising water; aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate. This combination of elements would specifically match the user's particular individual needs of making it possible to use the composition to clean the epidermis of a user. The above-described patents make no provision for a cleansing composition comprising water, aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate.

Therefore, a need exists for a new and improved cleansing composition comprising water; aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate. In this respect, the cleansing composition according to the present invention substantially departs from the conventional concepts and designs of the prior art, and in doing so provides an apparatus primarily developed for the purpose of making it possible to use the composition to clean the epidermis of a user.

SUMMARY OF THE INVENTION

The present composition, device, and associated method of using according to the principles of the present invention, overcomes the shortcomings of the prior art by providing a composition, a device and associated method of using the composition for use in cleaning the epidermis of a user is disclosed. The composition comprises water, aloe extract; citric acid; disodium EDTA; PEG-60 lanolin; potassium sorbate; propylene glycol; quatemium-52; SD-alcohol; benzethonium chloride; pumice; methychloridsothiazolinone; methylisothiazalinone; degreaser; triethanolamine; and tocopherylactate. The device comprises a pouch containing a towelette containing the composition of the present invention. The method of using comprises the steps of obtaining, opening, pulling, and wiping.

In view of the foregoing disadvantages inherent in the known type cleaning compositions now present in the prior art, the present invention provides an improved cleansing composition, which will be described subsequently in great detail, is to provide a new and improved cleansing composition which is not anticipated, rendered obvious, suggested, or even implied by the prior art, either alone or in any combination thereof.

To attain this, the present invention essentially comprises a composition comprising water, aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate.

There has thus been outlined, rather broadly, the more important features of the invention in order that the detailed description thereof that follows may be better understood, and in order that the present contribution of the art may be better appreciated.

The invention may also include a scent. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved cleansing composition that has all the advantages of the prior art cleansing composition and none of the disadvantages.

It is another object of the present invention to provide a new and improved cleansing composition that may be easily and efficiently manufactured and marketed.

An even further object of the present invention is to provide a new and improved cleansing composition that has a low cost of manufacture with regard to both materials and labor, and which accordingly is then susceptible of low prices of sale to the consuming public, thereby making such multipurpose storage unit and system economically available to the buying public.

Still another object of the present invention is to provide a new cleansing composition that provides in the apparatuses and methods of the prior art some of the advantages thereof, while simultaneously overcoming some of the disadvantages normally associated therewith.

Even still another object of the present invention is to provide a cleansing composition comprising water, aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate. This combination of elements makes it possible to use the composition to clean the epidermis of a user.

Yet another object of the present invention to provide a new and improved device containing the composition.

Lastly, it is an object of the present invention to provide a new and improved method of using comprises the steps of obtaining, opening, pulling, and wiping.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompany drawings and description matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an itemized listing of the ingredient contained in the composition in accordance with the principles of the present invention;

The same reference numerals refer to the same parts throughout the various figures.

DETAILED DESCRIPTION OF THE PREFERRED EMBODIMENT

Figure 2:
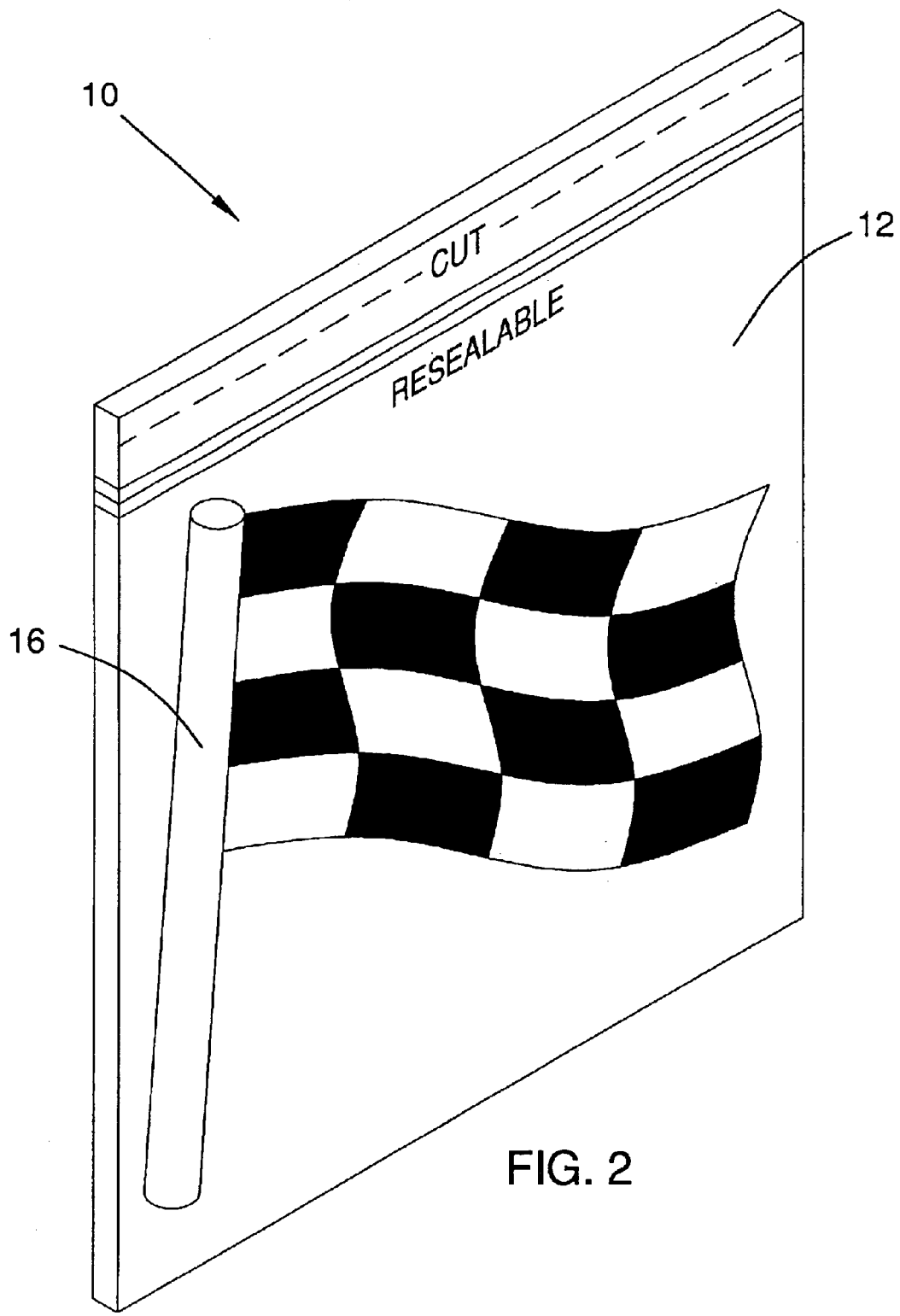
FIG. 2 is a perspective view of a preferred embodiment of the cleansing device of the present invention.

Referring now to the drawings, and in particular FIGS. 1 to 4 thereof, one preferred embodiment of the present invention is shown and generally designated by the reference numeral 10. One preferred embodiment of the composition for use is cleaning the epidermis of a user, the composition comprising: water; aloe extract; citric acid; disodium EDTA; PEG-60 lanolin; potassium sorbate; propylene glycol; quatemium-52; SD-alcohol; benzethonium chloride; pumice; methychloridsothiazolinone; methylisothiazalinone; degreaser, triethanolamine; and tocopherylactate.

An optional scent may be added to the composition. One preferred configuration of the scent is that it is in an amount ranging from about 0.1 to 10% by weight of the composition. A more preferred configuration of the scent is that it is in an amount ranging from about 3.0 to 5.0% by weight of the composition.

One preferred configuration of the composition comprises the water is in an amount ranging from about 1.0 to 40% by weight of the composition; the aloe extract is in an amount ranging from about 0.1 to 10% by weight of the composition; the citric acid is in an amount ranging from about 0.01 to 2.0% by weight of the composition; the disodium EDTA is in an amount ranging from about 0.1 to 10% by weight of the composition; the PEG-60 lanolin is in an amount ranging from about 0.1 to 10% by weight of the composition; the potassium sorbate is in an amount ranging from about 0.1 to 10% by weight of the composition; the propylene glycol is in an amount ranging from about 0.1 to 10% by weight of the composition; the quatemium-52 is in an amount ranging from about 0.1 to 10% by weight of the composition; the SD-alcohol is in an amount ranging from about 0.1 to 15% by weight of the composition; the benzethonium chloride is in an amount ranging from about 0.01 to 2.0% by weight of the composition; the pumice is in an amount ranging from about 0.1 to 10% by weight of the composition; the methychloridsothiazolinone is in an amount ranging from about 0.1 to 10% by weight of the composition; the methylisothiazalinone is in an amount ranging from about 0.1 to 10% by weight of the composition; the degreaser is in an amount ranging from about 0.1 to 10% by weight of the composition; the triethanolamine is in an amount ranging from about 0.1 to 10% by weight of the composition; and the tocopherylactate is in an amount ranging from about 0.1 to 10% by weight of the composition.

Another more preferred configuration of the composition comprises the water is in an amount ranging from about 20 to 25% by weight of the composition; the aloe extract is in an amount ranging from about 5.0 to 7.0% by weight of the composition; the citric acid is in an amount ranging from about 0.3 to 0.5% by weight of the composition; the disodium EDTA is in an amount ranging from about 3.0 to 5.0% by weight of the composition; the PEG-60 lanolin is in an amount ranging from about 3.0 to 5.0% by weight of the composition; the potassium sorbate is in an amount ranging from about 3.0 to 5.0% by weight of the composition; the propylene glycol is in an amount ranging from about 3.0 to 5.0% by weight of the composition; the quaternium-52 is in an amount ranging from about 3.0 to 5.0% by weight of the composition; the SD-alcohol is in an amount ranging from about 5.0 to 9.0% by weight of the composition; the benzethonium chloride is in an amount ranging from about 0.2 to 0.4% by weight of the composition; the pumice is in an amount ranging from about 3.0 to 5.0% by weight of the composition; the methychloridsothiazolinone is in an amount ranging from about 3.0 to 5.0% by weight of the composition; the methylisothiazalinone is in an amount ranging from about 3.0 to 5.0% by weight of the composition; the degreaser is in an amount ranging from about 3.0 to 5.0% by weight of the composition; the triethanolamine is in an amount ranging from about 3.0 to 5.0% by weight of the composition; and the tocopherylactate is in an amount ranging from about 3.0 to 5.0% by weight of the composition, in which this more; preferred configuration of the composition of may be further limited to the citric acid is in an amount ranging from about 0.4% by weight of the composition; the SD-alcohol is in an amount ranging from about 7.0% by weight of the composition; and the benzethonium chloride is in an; amount ranging from about 0.3% by weight of the composition.

A most preferred configuration of the composition comprises water is in an amount ranging from about 20 to 25% by weight of the composition; the aloe extract is in an amount ranging from about 5.0 to 7.0% by weight of the composition; the citric acid is in an amount ranging from about 0.4% by weight of the composition; the disodium EDTA is in an amount ranging from about 3.0 to 5.0% by weight of the composition; the PEG-60 lanolin is in an amount ranging from about 3.0 to 5.0% by weight of the composition; the potassium sorbate is in an amount ranging from about 3.0 to 5.0% by weight of the composition; the propylene glycol is in an amount ranging from about 3.0 to 5.0% by weight of the composition; the quatemium-52 is in an amount ranging from about 3.0 to 5.0% by weight of the composition; the SD-alcohol is in an amount ranging from about 7.0% by weight of the composition; the benzethonium chloride is in an amount ranging from about 0.3% by weight of the composition; the pumice is in an amount ranging from about 3.0 to 5.0% by weight of the composition; the methychloridsothiazolinone is in an amount ranging from about 3.0 to 5.0% by weight of the composition; the methylisothiazalinone is in an amount ranging from about 3.0 to 5.0% by weight of the composition; the degreaser is in an amount ranging from about 3.0 to 5.0% by weight of the composition; the triethanolamine is in an amount ranging from about 3.0 to 5.0% by weight of the composition; the tocopherylactate is in an amount ranging from about 3.0 to 5.0% by weight of the composition; and the scent is in an amount ranging from about 3.0 to 5.0% by weight of the composition.

One preferred embodiment of the device 10 holding a composition for use is cleaning the epidermis of a user, the device 10 comprising: a resealable zip lock pouch 12; and at least one paper based towelette 14 stored within the reseable zip lock pouch 12, the paper based towelette 14 containing the composition comprising: water, aloe extract; citric acid; disodium EDTA; PEG-60 lanolin; potassium sorbate; propylene glycol; quatemium-52; SD-alcohol; benzethonium chloride; pumice; methychloridsothiazolinone; methylisothiazalinone; degreaser; triethanolamine; and tocopherylactate.

An optional insignia 16 may be added to the device 10. The insignia 16 is embossed on the resealable zip lock pouch 12. One preferred configuration of the insignia 16 is that it is an image of a checkered flag.

An optional decoration 18 may be added to the device 10. The decoration 18 is printed on each paper-based towelette 14. One preferred configuration of the decoration 18 is an image of a checkerboard.

An optional plurality of towelettes 14 may be added to the device 10. One preferred configuration of the number of towelettes 14 contained in the device comprises three paper based towelettes 14.

One preferred embodiment of the method of using a device 10 holding a composition for use is cleaning the epidermis of a user, the method comprises the steps of obtaining, opening, pulling, and wiping. The obtaining step comprises obtaining the device 10 comprising: a resealable zip lock pouch 12; and at least one paper based towelette 14 stored within the resealable zip lock pouch 12, the paper based towelette 14 containing the composition comprising: water is in an amount ranging from about 20 to 25% by weight of composition; aloe extract is in an amount ranging from about 5.0 to 7.0% by weight of composition; citric acid is in an amount ranging from about 0.4% by weight of composition; disodium EDTA is in an amount ranging from about 3.0 to 5.0% by weight of composition; PEG-60 lanolin is in an amount ranging from about 3.0 to 5.0% by weight of composition; potassium sorbate is in an amount ranging from about 3.0 to 5.0% by weight of composition; propylene glycol is in an amount ranging from about 3.0 to 5.0% by weight of composition; quaternium-52 is in an amount ranging from about 3.0 to 5.0% by weight of composition; SD-alcohol is in an amount ranging from about 7.0% by weight of composition; benzethonium chloride is in an amount ranging from about 0.3% by weight of composition; pumice is in an amount ranging from about 3.0 to 5.0% by weight of composition; methychloridsothiazolinone is in an amount ranging from about 3.0 to 5.0% by weight of composition; methylisothiazalinone is in an amount ranging from about 3.0 to 5.0% by weight of composition; degreaser is in an amount ranging from about 3.0 to 5.0% by weight of composition; triethanolamine is in an amount ranging from about 3.0 to 5.0% by weight of composition; tocopherylactate is in an amount ranging from about 3.0 to 5.0% by weight of composition; and scent is in an amount ranging from about 3.0 to 5.0% by weight of composition. The opening step comprises opening up the resealable zip lock pouch 12 of the device 10. The pulling step comprises pulling out the paper based towelette 14 from the opened up resealable zip lock pouch 12 of the device 10. The wiping step comprises wiping the skin of the user with the pulled out paper based towelette 14.

Referring now to FIG. 1 which depicts an itemized listing of the ingredient contained in the composition shows that the composition comprises water, aloe extract; citric acid; disodium EDTA; PEG-60 lanolin; potassium sorbate; propylene glycol; quatemium-52; SD-alcohol; benzethonium chloride; pumice; methychloridsothiazolinone; methylisothiazalinone; degreaser; triethanolamine; and tocopherylactate.

Referring now to FIG. 2 which depicts a perspective view of a preferred embodiment of the cleansing device 10 showing the resealable zip lock pouch 12 with a race flag insignia embossed on the pouch 12.

Figure 3:
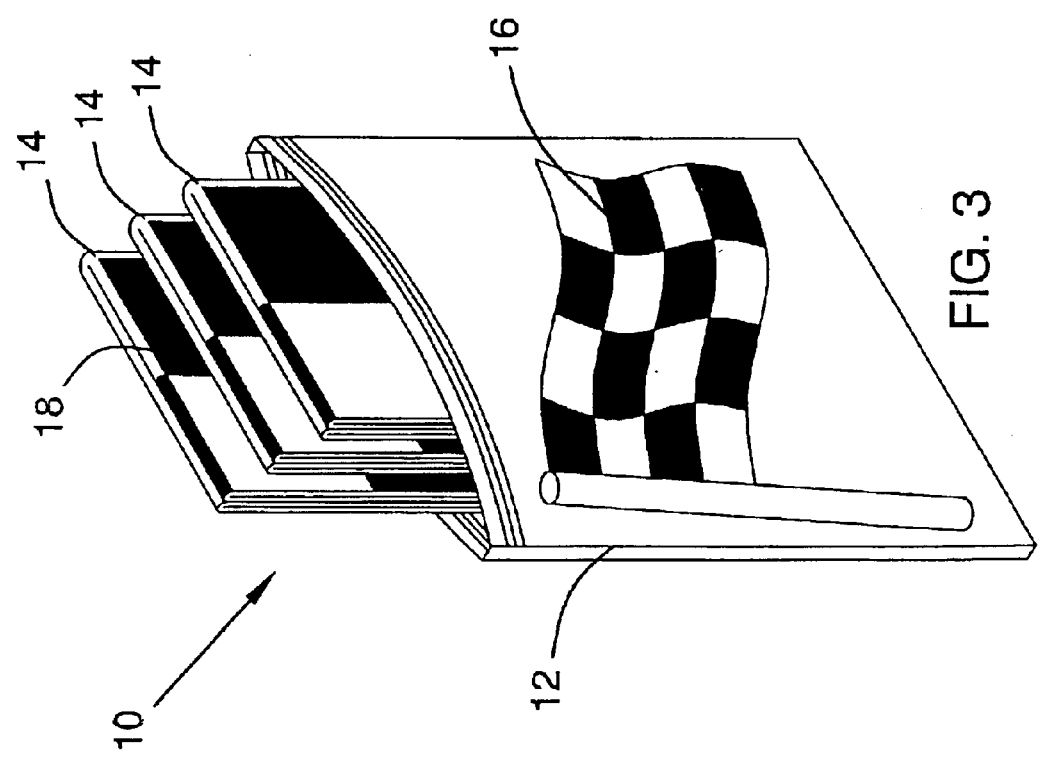
FIG. 3 is a perspective view of a preferred embodiment of the cleansing device of the present invention.

Referring now to FIG. 3 which depicts a perspective view of a preferred embodiment of the cleansing device 10 showing three folded towelettes 14 having checker board decorations 18 printed on the towelettes 14. Also shown is the resealable zip lock pouch 12 with a race flag insignia embossed on the pouch 12.

Figure 4:
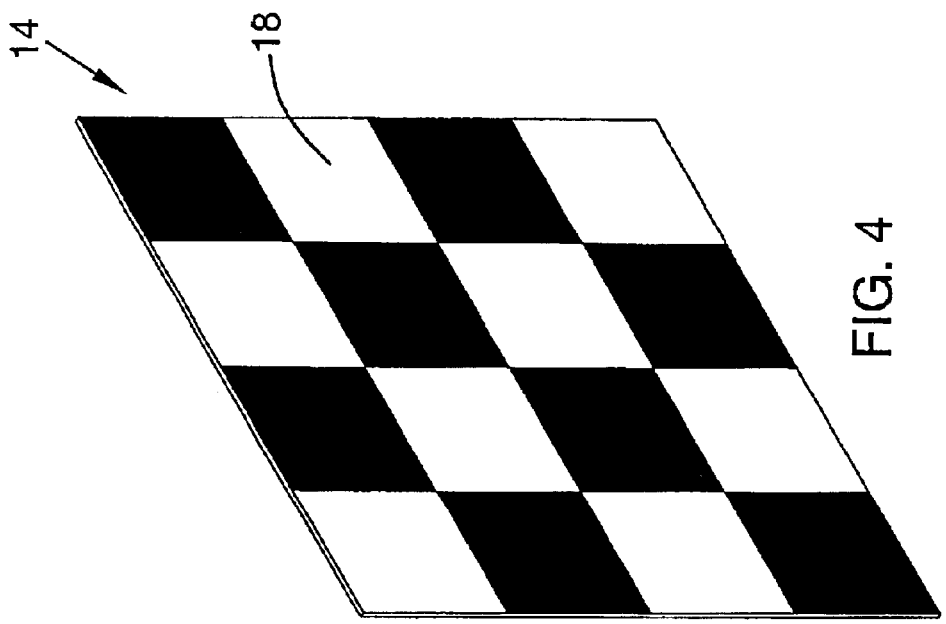
FIG. 4 is a perspective view of a preferred embodiment of the towelette of the cleansing device of the present invention.

Referring now to FIG. 4 which depicts a perspective view of a preferred embodiment of the towelette of the cleansing device 10 showing the unfolded towelette 14 having a checker board decoration 18 printed on the towelette 14.

The same reference numerals refer to the same parts throughout the various figures.

As to the manner of usage and operation of the present invention, the same should be apparent from the above description. Accordingly, no further discussion relating to the manner of usage and operation will be provided.

While a preferred embodiment of the cleansing composition has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or comprising" or the term "includes or variations, thereof, or the them "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combination any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A composition for use is cleaning the epidermis of a user, said composition comprising: water; aloe extract; citric acid; disodium EDTA; PEG-60 lanolin; potassium sorbate; propylene glycol; quaternium-52; SD-alcohol; benzethonium chloride; pumice; methychloridsothiazolinone; methylisothiazalinone; degreaser; triethanolamine; and tocopherylactate.

2. The composition of claim 1 further comprising a scent.

3. The composition of claim 1 wherein said water is in an amount ranging from about. 1.0 to 40% by weight of said composition; said aloe extract is in an amount ranging from about 0.1 to 10% by weight of said composition; said citric acid is in an amount ranging from about 0.01 to 2.0% by weight of said composition; said disodium EDTA is in an amount ranging from about 0.1 to 10% by weight of said composition; said PEG-60 lanolin is in an amount ranging from about 0.1 to 10% by weight of said composition; said potassium sorbate is in an amount ranging from about 0.1 to 10% by weight of said composition; said propylene glycol is in an amount ranging from about 0.1 to 10% by weight of said composition; said quaternium-52 is in an amount ranging from about 0.1 to 10% by weight of said composition; said SD-alcohol is in an amount ranging from about 0.1 to 15% by weight of said composition; said benzethonium chloride is in an amount ranging from about 0.01 to 2.0% by weight of said composition; said pumice is in an amount ranging from about 0.1 to 10% by weight of said composition; said methychloridsothiazolinone is in an amount ranging from about 0.1 to 10% by weight of said composition; said methylisothiazalinone is in an amount ranging from about 0.1 to 10% by weight of said composition; said degreaser is in an amount ranging from about 0.1 to 10% by weight of said composition; said triethanolamine is in an amount ranging from about 0.1 to 10%: by weight of said composition; and said tocopherylactate is in an amount ranging from about 0.1 to 10% by weight of said composition.

4. The composition of claim 3 wherein said water is in an amount ranging from about 20 to 25% by weight of said composition; said aloe extract is in an amount ranging from about 5.0 to 7.0% by weight of said composition; said citric acid is in an amount ranging from about 0.3 to 0.5% by weight of said composition; said disodium EDTA is in an amount ranging from about 3.0 to 5.0% by weight of said composition; said PEG-60 lanolin is in an amount ranging from about 3.0 to 5.0% by weight of said composition; said potassium sorbate is in an amount ranging from about 3.0 to 5.0% by weight of said composition; said propylene glycol is in an amount ranging from about 3.0 to 5.0% by weight of said composition; said quaternium-52 is in an amount ranging from about 3.0 to 5.0% by weight of said composition; said SD-alcohol is in an amount ranging from about 5.0 to 9.0% by weight of said composition; said benzethonium chloride is in an amount ranging from about 0.2 to 0.4% by weight of said composition; said pumice is in an amount ranging from about 3.0 to 5.0% by weight of said composition; said methychloridsothiazolinone is in an amount ranging from about 3.0 to 5.0% by weight of said composition; said methylisothiazalinone is in an amount ranging from about 3.0 to 5.0% by weight of said composition; said degreaser is in an amount ranging from about 3.0 to 5.0% by weight of said composition; said triethanolamine is in an amount ranging from about 3.0 to 5.0% by weight of said composition; and said tocopherylactate is in an amount ranging from about 3.0 to 5.0% by weight of said composition.

5. The composition of claim 4 wherein said citric acid is in an amount ranging from about 0.4% by weight of said composition; said SD-alcohol is in an amount ranging from about 7.0% by weight of said composition; and said benzethonium chloride is in an amount ranging from about 0.3% by weight of said composition.

6. The composition of claim 2 wherein said scent is in an amount ranging from about 0.1 to 10% by weight of said composition.

7. The composition of claim 6 wherein said scent is in an amount ranging from about 3.0 to 5.0% by weight of said composition.

8. The composition of claim 7 wherein said water is in an amount ranging from about 20 to 25% by weight of said composition; said aloe extract is in an amount ranging from about 5.0 to 7.0% by weight of said composition; said citric acid is in an amount ranging from about 0.4% by weight of said composition; said disodium EDTA is in an amount ranging from about 3.0 to 5.0% by weight of said composition; said PEG-60 lanolin is in an amount ranging from about 3.0 to 5.0% by weight of said composition; said potassium sorbate is in an amount ranging from about 3.0 to 5.0% by weight of said composition; said propylene glycol is in an amount ranging from about 3.0 to 5.0% by weight of said composition; said quatemium-52 is in an amount ranging from about 3.0 to 5.0% by weight of said composition; said SD-alcohol is in an amount ranging from about 7.0% by weight of said composition; said benzethonium chloride is in an amount ranging from about 0.3% by weight of said composition; said pumice is in an amount ranging from about 3.0 to 5.0% by weight of said composition; said methychloridsothiazolinone is in an amount ranging from about 3.0 to 5.0% by weight of said composition; said methylisothiazalinone is in an amount ranging from about 3.0 to 5.0% by weight of said composition; said degreaser is in an amount ranging from about 3.0 to 5.0% by weight of said composition; said triethanolamine is in an amount ranging from about 3.0 to 5.0% by weight of said composition; said tocopherylactate is in an amount ranging from about 3.0 to 5.0% by weight of said composition; and said scent is in an amount ranging from about 3.0 to 5.0% by weight of said composition.

9. A device holding a composition for use is cleaning the epidermis of a user, said device comprising: a resealable zip lock pouch; and at least one paper based towelette stored within said reseable zip lock pouch, said paper based towelette containing the composition comprising: water; aloe extract; citric acid; disodium EDTA; PEG-60 lanolin; potassium sorbate; propylene glycol; quatemium-52; SD-alcohol; benzethonium chloride; pumice; methychloridsothiazolinone; methylisothiazalinone; degreaser; triethanolamine; and tocopherylactate.

10. The device of claim 9 further comprising an insignia embossed on said resealable zip lock pouch.

11. The device of claim 10 wherein said insignia is an image of a checkered flag.

12. The device of claim 9 further comprising a decoration printed on each of paper based towelette.

13. The device of claim 12 wherein said decoration is an image of a checker board.

14. The device of claim 9 further comprising three paper based towelettes.

15. The device of claim 9 wherein the composition further comprising a scent.

16. The device of claim 9 wherein the composition comprising: said water is in an amount ranging from about 20 to 25% by weight of said composition; said aloe extract is in an amount ranging from about 5.0 to 7.0% by weight of said composition; said citric acid is in an amount ranging from about 0.4% by weight of said composition; said disodium EDTA is in an amount ranging from about 3.0 to 5.0% by weight of said composition; said PEG-60 lanolin is in an amount ranging from about 3.0 to 5.0% by weight of said composition; said potassium sorbate is in an amount ranging from about 3.0 to 5.0% by weight of said composition; said propylene glycol is in an amount ranging from about 3.0 to 5.0% by weight of said composition; said quaternium-52 is in an amount ranging from about 3.0 to 5.0% by weight of said composition; said SD-alcohol is in an amount ranging from about 7.0% by weight of said composition; said benzethonium chloride is in an amount ranging from about 0.3% by weight of said composition; said pumice is in an amount ranging from about 3.0 to 5.0% by weight of said composition; said methychloridsothiazolinone is in an amount ranging from about 3.0 to 5.0% by weight of said composition; said methylisothiazalinone is in an amount ranging from about 3.0 to 5.0% by weight of said composition; said degreaser is in an amount ranging from about 3.0 to 5.0% by weight of said composition; said triethanolamine is in an amount ranging from about 3.0 to 5.0% by weight of said composition; and said tocopherylactate is in an amount ranging from about 3.0 to 5.0% by weight of said composition.

17. The device of claim 15 wherein the composition comprising said water is in an amount ranging from about 20 to 25% by weight of said composition; said aloe extract is in an amount ranging from about 5.0 to 7.0% by weight of said composition; said citric acid is in an amount ranging from about 0.4% by weight of said composition; said disodium EDTA is in an amount ranging from about 3.0 to 5.0% by weight of said composition; said PEG-60 lanolin is in an amount ranging from about 3.0 to 5.0% by weight of said composition; said potassium sorbate is in an amount ranging from about 3.0 to 5.0% by weight of said composition; said propylene glycol is in an amount ranging from about 3.0 to 5.0% by weight of said composition; said quaternium-52 is in an amount ranging from about 3.0 to 5.0% by weight of said composition; said SD-alcohol is in an amount ranging from about 7.0% by weight of said composition; said benzethonium chloride is in an amount ranging from about 0.3% by weight of said composition; said pumice is in an amount ranging from about 3.0 to 5.0% by weight of said composition; said methychloridsothiazolinone is in an amount ranging from about 3.0 to 5.0% by weight of said composition; said methylisothiazalinone is in an amount ranging from about 3.0 to 5.0% by weight of said composition; said degreaser is in an amount ranging from about 3.0 to 5.0% by weight of said composition; said triethanolamine is in an amount ranging from about 3.0 to 5.0% by weight of said composition; said tocopherylactate is in an amount ranging from about 3.0 to 5.0% by weight of said composition; and said scent is in an amount ranging from about 3.0 to 5.0% by weight of said composition.

18. The device of claim 9 wherein said towelette is generally square in shape.

19. The device of claim 18 wherein said towelette is about 12 inches wide by about 12 inches long.

20. A method of using a device holding a composition for use is cleaning the epidermis of a user, said method comprising:

obtaining the device comprising: a resealable zip lock pouch; and at cast one paper based towelette stored within said resealable zip lock pouch, said paper based towelette containing the composition comprising: water is in an amount ranging from about 20 to 25% by weight of composition; aloe extract is in an amount ranging from about 5.0 to 7.0% by weight of composition; citric acid is in an amount ranging from about 0.4% by weight of composition; disodium EDTA is in an amount ranging from about 3.0 to 5.0% by weight of composition; PEG-60 lanolin is in an amount ranging from about 3.0 to 5.0% by weight of composition; potassium sorbate is in an amount ranging from about 3.0 to 5.0% by weight of composition; propylene glycol is in an amount ranging from about 3.0 to 5.0% by weight of composition; quatemium-52 is in an amount ranging from about 3.0 to 5.0% by weight of composition; SD-alcohol is in an amount ranging from about 7.0% by weight of composition; benzethonium chloride is in an amount ranging from about 0.3% by weight of composition; pumice is in an amount ranging from about 3.0 to 5.0% by weight of composition; methychloridsothiazolinone is in an amount ranging from about 3.0 to 5.0% by weight of composition; methylisothiazalinone is in an amount ranging from about 3.0 to 5.0% by weight of composition; degreaser is in an amount ranging from about 3.0 to 5.0% by weight of composition; triethanolamine is in an amount ranging from about 3.0 to 5.0% by weight of composition; tocopherylactate is in an amount ranging from about 3.0 to 5.0% by weight of composition; and scent is in an amount ranging from about 3.0 to 5.0% by weight of composition;

opening up the resealable zip lock pouch of the device;

pulling out the paper based towelette from the opened up resealable zip lock pouch of the device; and wiping the skin of the user with the pulled out paper based towelette.

\* \* \* \* \*